United States Patent

Mederski et al.

[11] Patent Number: 5,321,137
[45] Date of Patent: Jun. 14, 1994

[54] PROCESS FOR THE PREPARATION OF IMIDAZOPYRIDINES

[75] Inventors: Werner Mederski, Erzhausen; Heinz-Hermann Bokel, Darmstadt, both of Fed. Rep. of Germany

[73] Assignee: Merck Patent Gesellschaft mit beschrankter Haftung, Darmstadt, Fed. Rep. of Germany

[21] Appl. No.: 102,175

[22] Filed: Aug. 4, 1993

[30] Foreign Application Priority Data

Aug. 5, 1992 [DE] Fed. Rep. of Germany ....... 4225835

[51] Int. Cl.$^5$ .................. C07D 213/75; C07D 471/04
[52] U.S. Cl. ..................................... 546/118; 546/308
[58] Field of Search ................................ 546/308, 118

[56] References Cited

U.S. PATENT DOCUMENTS 5,138,069  8/1992  Carini et al. ...................... 548/253

FOREIGN PATENT DOCUMENTS 399731  11/1990  European Pat. Off. .
505893   9/1992  European Pat. Off. .

OTHER PUBLICATIONS

Stetsenko et al., Ukrainskii Khimicheskii Zhurnal, vol. 39 (7), pp. 703-707 (1973) (Eng. Translation).

Primary Examiner—Bernard Dentz
Attorney, Agent, or Firm—Millen, White, Zelano & Branigan

[57] ABSTRACT

The invention relates to a novel process for the preparation of imidazopyridines of formula I:

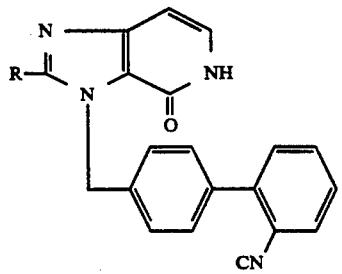

in which
R is an alkyl having 1-6 C atoms, characterized in that 3,4-diamino-2-chloropyridine (II) is reacted with an acid anhydride of the formula RCO—O—COR 40 (III), in which R is as defined and R' is R or can be another aliphatic or aromatic radical, to give a 4-amino-2-chloro-3-R-CO-aminopyridine (IV), this is converted with 4'-bromomethyl-2-cyanobiphenyl (V), in the presence of an alkali metal alcoholate in an inert solvent, to a 4-amino-2-chloro-3-R-CO-[N-(2'-cyano-biphenyl-4-ylmethyl)-amino]pyridine (VI) and this is treated with a strong acid, a 2-R-4-chloro-3-(2'-cyano-biphenyl-4-ylmethyl)-3H-imidazo[4,5-c]pyridine (VII) being formed as an intermediate.

16 Claims, No Drawings

PROCESS FOR THE PREPARATION OF IMIDAZOPYRIDINES

SUMMARY OF THE INVENTION

The invention relates to a novel process for the preparation of imidazopyridines of formula I:

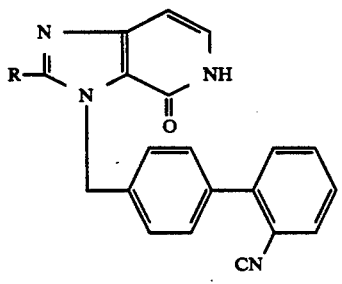

in which

R is alkyl having 1-6 C atoms, characterized in that 3,4-diamino-2-chloropyridine (II) is reacted with an acid anhydride of the formula RCO—O—COR' (III), in which R is as defined and R' is R or can be another aliphatic or aromatic radical, to give a 4-amino-2-chloro-3-R-CO-aminopyridine (IV), this is converted with 4'-bromomethyl-2-cyanobiphenyl (V), in the presence of an alkali metal alcoholate in an inert solvent, to a 4-amino-2-chloro-3-R-CO-[N-(2'-cyanobiphenyl-4-ylmethyl)amino]pyridine (VI) with 2-R-4-chloro-3-(2'-cyanobiphenyl-4-ylmethyl)-3H-imidazo[4,5-c]pyridine (VII) being formed from (VI) as an intermediate, and (VI) and/or (VII) is treated with a strong acid to obtain a compound of formula I.

Compounds of formula I inhibit the action of angiotensin II and accordingly can be used as pharmaceutical active ingredients, especially for lowering the blood pressure. They are also suitable as intermediates for the preparation of other pharmaceutical active ingredients.

The radical R is preferably linear and is preferably butyl or propyl, or else methyl, ethyl, pentyl, hexyl, isopropyl, isobutyl, sec-butyl, tert-butyl, 1-, 2- or 3-methylbutyl, 1,1-, 1,2- or 2,2-dimethylpropyl, 1-, 2-, 3- or 4-methylpentyl, 1- or 2-ethylbutyl, 1,1- , 1,2-, 1,3-, 2,2-, 2,3- or 3,3-dimethylbutyl or 1,1,2- or 1,2,2,- trimethylpropyl.

The radical R' is preferably R, in which case II is the anhydride of a (single) acid. However, the radical R' can also be another aliphatic or aromatic radical, in which case II is a "mixed" acid anhydride. Here R' is preferably an aliphatic or aromatic hydrocarbon radical having up to 20 C atoms, especially up to 10 C atoms, in each case, for example, alkyl, especially branched alkyl such as tert-butyl, or phenyl which is unsubstituted or substituted by 1-5 $C_{1-3}$-alkyl groups, especially methyl, such as 3,5-dimethylphenyl or 2,4,6-trimethylphenyl.

The conversion of a 3,4-diaminopyridine to a 2-R-imidazo[4,5-c]pyridine is conventionally carried out by reaction with an acid of the formula R-COOH in the presence of polyphosphoric acid or $POCl_3$ at relatively high temperatures. If, for example, II is reacted with valeric acid in the presence of polyphosphoric acid at 100°-180°, 2-butyl-4,5-dihydro-4-oxo-1(or 3)H-imidazo[4,5-c]pyridine is obtained as the main product, with simultaneous hydrolysis of the Cl atom. This has the disadvantage that a mixture of products is formed in the "alkylation" with V.

An object of the invention is to avoid this disadvantage of the conventional procedure and to find a process in which—at any stage—the "alkylation" with V takes place selectively in the desired position. This object is achieved by the claimed process.

Upon further study of the specification and appended claims, further objects and advantages of this invention will become apparent to those skilled in the art.

In fact, if II is reacted with an acid anhydride III, IV is obtained selectively in high yield. This reaction is preferably carried out under relatively mild conditions in the presence of an inert solvent or solvent mixture at temperatures of preferably about 0–100°, especially 10°–50°, preferably under normal pressure, for preferably about 1–72 hours using III in the calculated amount, in other words not in excess. An example of a suitable solvent is an ether such as tetrahydrofuran (THF) or dioxane.

According to the invention, the reaction of IV with V (known from EP 253 310, Example 89) is performed in an inert solvent or solvent mixture, preferably a polar solvent, for example an amide such as dimethylformamide or a lactam such as N-methylpyrrolidone (NMP), in the presence of a base, preferably an alkali metal alcoholate such as potassium tert-butylate or else sodium or potassium methylate or ethylate.

The reaction is preferably carried out at temperatures of about 0°–50°, especially 10°–20°, preferably under normal pressure, for preferably about 1–72 hours, the procedure being firstly to deprotonate IV with the alcoholate and then to add a solution of V dropwise. Surprisingly, under these conditions, VI is obtained selectively as the main product and VII, formed therefrom by the elimination of water as a by-product.

The resulting VI (or VII or a mixture of VI and VII), with or without isolation, is then treated with a strong acid, preferably a strong mineral acid such as hydrochloric acid or sulfuric acid, and preferably in the presence of an additional inert solvent or solvent mixture, for example water/NMP, conveniently at temperatures of preferably about 0°–110°, especially 100°–110°, preferably under normal pressures, and preferably for about 1 hour–7 days. VI is thereby cyclized to VII and the chlorine atom is also eliminated by hydrolysis.

It is also possible to combine several steps so that intermediate products are not isolated. In particular, one can carry out the reaction of IV with V to VI or VII, respectively, and the following elimination of the chlorine atom in one step; VI and VII are not isolated in that case.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 42 25 835.9, are hereby incorporated by reference.

EXAMPLES

Example 1

(a) 186 g of valeric anhydride are added dropwise to a solution of 143.5 g of 3,4-diamino-2-chloropyridine in 1350 ml of THF and the mixture is stirred for 16 hours at 20°. 1 l of saturated NaHCO₃ solution and 340 ml of saturated Na₂CO₃ solution are added. The mixture is filtered, the filtrate is extracted with ethyl acetate and the extract is dried over Na₂SO₄ and evaporated to give 4-amino-2-chloro-3-valeramidopyridine, (IVa), m.p. 163°, yield: 192 g.

(b) a solution of 36.8 g of potassium tert-butylate in 100 ml of NMP is added dropwise at 10°–15° to a solution of 64.9 g of IVa in 300 ml of NMP, with stirring.

After stirring for a further half an hour, 85.2 g of V in 300 ml of NMP are added dropwise at 10°–15°. After stirring for a further 16 hours, the mixture is worked up with ethyl acetate and saturated NaCl solution. Crystallization of the crude product from ethyl acetate/tert-butyl methyl ether gives 40 g of 4-amino-2-chloro-3-N-(2'-cyanobiphenyl-4-ylmethyl)valeramidopyridine (VIa), m.p. 144°. A further 13.7 g of 2-butyl-4-chloro-3-(2'-cyanobiphenyl-4-ylmethyl)-3H-imidazo[4,5-c]pyridine (VIIa), m.p. 133.5°, can be obtained from the mother liquor by recrystallization.

(c) A mixture of 43.1 g of (VIa), 36.2 g of VIIa, 2000 ml of 15% hydrochloric acid and 1200 ml of NMP is stirred at 105° for 48 hours. It is cooled, the pH is adjusted to 9 with sodium hydroxide solution, the mixture is extracted with ethyl acetate and the extract is filtered, washed with water and dried over Na₂SO₄ to give 64 g of 2-butyl-3-(2'-cyanobiphenyl-4-ylmethyl)-4,5-dihydro-4-oxo-3H-imidazo[4,5-c]pyridine (Ia), m.p. 165°.

Example 2

A solution of 227.7 g of IVa in 1000 ml of NMP is prepared under N₂, a solution of 129.1 g of K-tert.-butylate in 400 ml of NMP is added dropwise with stirring at 5–10°, stirring is continued for one hour and a solution of 299.4 g of V in 750 ml of NMP is added dropwise with stirring at 5–10°. After 5 hours stirring at 20°, 3100 ml of 18% hydrochloric acid is added, and the mixture is warmed to 105° for 40 hours. The mixture is then cooled to 80° and 3700 ml of 16% sodium hydroxide solution is added dropwise. The mixture is cooled, the precipitated Ia is filtered off, washed with water and recrystallized from ethanol/water 1:1; 316 g of pure Ia, m.p. 165°, are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of imidazopyridines of formula I:

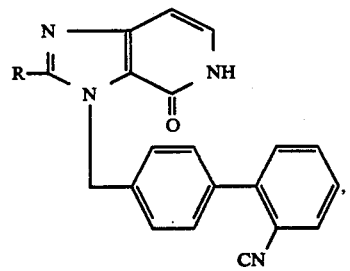

wherein R is alkyl having 1–6 C atoms, said process comprising:

reacting 3,4-diamino-2-chloropyridine with an acid anhydride of the formula RCO-O-COR' in which R is as defined and R' is R or another aliphatic or aromatic radical, to give 4-amino-2-chloro-3-R-CO-aminopyridine;

reacting said 4-amino-2-chloro-3-R-CO-aminopyridine with 4'-bromomethyl-2-cyano-biphenyl in the presence of an alkali metal alcoholate in an inert solvent, to obtain 4-amino-2-chloro-3-R-CO-[N-(2'-cyano -biphenyl-4-ylmethyl)amino]pyridine and, as an intermediate formed therefrom, 2-R-4-chloro-3-(2'-cyano-biphenyl-4-ylmethyl)-3H-imidazo[4,5-c]pyridine;

treating said 4-amino-2-chloro-3-R-CO-[N-(2'-cyano-biphenyl-4-ylmethyl)amino]pyridine, said 2-R-4-chloro-3-(2'-cyano-biphenyl-4-ylmethyl)-3H-imidazo [4,5-c]pyridine, or a mixture thereof with an acid to obtain a compound of formula I.

2. A process according to claim 1, wherein R' is an aliphatic or aromatic hydrocarbon having, in each case, up to 20 C atoms.

3. A process according to claim 1, wherein R' is an alkyl having up to 10C atoms, unsubstituted phenyl or phenyl substituted by 1–5 C₁₋₃-alkyl groups.

4. A process according to claim 2 wherein R' is the same as R.

5. A process according to claim 1, wherein the reaction of 3,4-diamino-2-chloropyridine with said acid anhydride is conducted at a temperature of 0°–100° C. in the presence of an inert solvent.

6. A process according to claim 5, wherein the reaction of 3,4-diamino-2-chloropyridine with said acid anhydride is conducted at a temperature of 10°–50° C.

7. A process according to claim 5, wherein said inert solvent is tetrahydrofuran or dioxane.

8. A process according to claim 1, wherein said reaction of 4-amino-2-chloro-3-R-CO-aminopyridine with 4'-bromomethyl-2-cyanobiphenyl is performed in an inert solvent at a temperature of 0°–50° C.

9. A process according to claim 8, wherein said reaction of 4-amino-2-chloro-3-R-CO-aminopyridine with 4'-bromomethyl-2-cyanobiphenyl is conducted at a temperature of 10°–20° C.

10. A process according to claim 1, wherein said alkali metal alcoholate is potassium tert-butylate, sodium methylate, potassium methylate, sodium ethylate, or potassium ethylate.

11. A process according to claim 1, wherein treatment of said 4-amino-2-chloro-3-R-CO-[N-(2-cyanobiphenyl-4-ylmethyl)amino]pyridine and/or 2-R-4-chloro-3-(2'-cyanobiphenyl-4-ylmethyl)-3H-imidazo[4,5-c]pyridine with an acid is conducted at a temperature of 0°–110° C.

12. A process according to claim 11, wherein said acid is hydrochloric acid or sulfuric acid.

13. A process according to claim 11, wherein said temperature is 100°–110° C.

14. A process according to claim 11, wherein said treatment with an acid is conducted in the presence of an inert solvent or inert solvent mixture.

15. A process according to claim 1, wherein said compound of formula I is 2-butyl-3-(2′-cyanobiphenyl-4-yl-methyl)-4,5-dihydro -4-oxo-3H-imidazo [4,5-C]pyridine.

16. A process for the production of 4-amino-2-chloro-3-R-CO-aminopyridine wherein R is $C_{1-6}$-alkyl, said process comprising reacting 3,4-diamino-2-chloropyridine with an acid anhydride of the formula RCO—O—COR′ wherein R is as defined and R′ is R or another aliphatic or aromatic radical.

* * * * *